United States Patent
Karmaker et al.

(10) Patent No.: US 6,186,790 B1
(45) Date of Patent: *Feb. 13, 2001

(54) PREFABRICATED COMPONENTS FOR DENTAL APPLIANCES

(75) Inventors: Ajit Karmaker, Wallingford; Martin L. Schulman, Orange; Arun Prasad, Cheshire, all of CT (US)

(73) Assignee: Jeneric/Pentron Incorporated, Wallingford, CT (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/190,806

(22) Filed: Nov. 12, 1998

Related U.S. Application Data

(63) Continuation-in-part of application No. 09/059,492, filed on Apr. 13, 1998, now abandoned.

(51) Int. Cl.$^7$ .................................................. A61C 13/12
(52) U.S. Cl. ............................................. 433/215; 433/180
(58) Field of Search ................................. 433/180, 181, 433/190, 215, 224

(56) References Cited

U.S. PATENT DOCUMENTS

| | | | |
|---|---|---|---|
| 3,066,112 | 11/1962 | Bowen | 260/41 |
| 3,179,623 | 4/1965 | Bowen | 260/47 |
| 3,194,784 | 7/1965 | Bowen | 260/41 |
| 3,751,399 | 8/1973 | Lee, Jr. et al. | 268/17 |
| 3,926,906 | 12/1975 | Lee, II et al. | 260/42.53 |
| 4,457,714 * | 7/1984 | Klein | 433/180 |
| 4,544,359 | 10/1985 | Waknine | 523/115 |
| 4,547,531 | 10/1985 | Waknine | 523/116 |
| 4,717,341 | 1/1988 | Goldberg et al. | 433/9 |
| 4,735,571 * | 4/1988 | Salvo | 433/215 |
| 4,775,320 * | 10/1988 | Marshall et al. | 433/180 |
| 4,877,400 * | 10/1989 | Holsclaw | 433/183 |
| 4,894,012 * | 1/1990 | Goldberg et al. | 433/215 |
| 5,098,304 * | 3/1992 | Scharf | 433/215 |
| 5,120,224 * | 6/1992 | Golub | 433/215 |
| 5,276,068 | 1/1994 | Waknine | 522/28 |
| 5,360,482 * | 11/1994 | Belvedere | 118/404 |
| 5,444,104 | 8/1995 | Waknine | 522/24 |
| 5,545,039 * | 8/1996 | Mushabac | 433/218 |
| 5,564,929 * | 10/1996 | Alpert | 433/224 |
| 5,684,103 | 11/1997 | Jia et al. | 526/218.1 |
| 5,772,438 * | 6/1998 | Deom | 433/181 |
| 5,797,748 * | 8/1998 | Reynaud et al. | 433/224 |
| 5,816,816 * | 10/1998 | Scharf | 433/224 |
| 5,846,640 * | 12/1998 | Vallittu | 428/306.6 |
| 5,921,778 * | 7/1999 | Karmaker et al. | 433/215 |
| 6,013,694 * | 1/2000 | Jia et al. | 523/116 |
| 6,030,220 * | 2/2000 | Karmaker et al. | 433/215 |
| 6,039,569 * | 3/2000 | Prasad et al. | 433/180 |

FOREIGN PATENT DOCUMENTS

WO/94/08783 * 4/1994 (WO) .................................... 433/180

* cited by examiner

*Primary Examiner*—Ralph A. Lewis
(74) *Attorney, Agent, or Firm*—Ann M. Knab

(57) ABSTRACT

Ready-to-use preshaped, prefabricated cured structural components are prepared in a variety of shapes and sizes to be used in the fabrication of dental appliances. Preferably the structural components are fabricated of a fiber-reinforced composite material comprising fibers impregnated with a polymeric matrix. The polymeric matrix is partially or fully cured to the point of sufficient hardness to provide a ready-to-use structural component for use in the fabrication of dental appliances such as orthodontic retainers, bridges, space maintainers, tooth replacement appliances, splints, crowns, partial crowns, dentures, posts, teeth, jackets, inlays, onlays, facings, veneers, facets, implants, abutments, cylinders, and connectors.

33 Claims, 2 Drawing Sheets

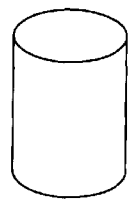
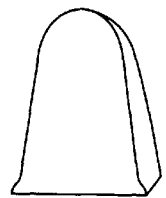
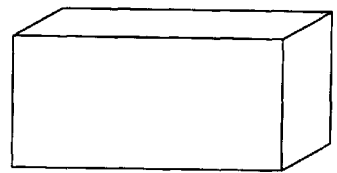
FIG. 7        FIG. 8        FIG. 9
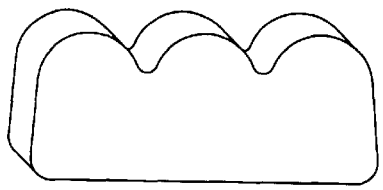
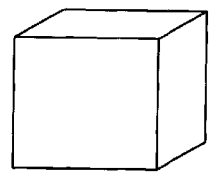
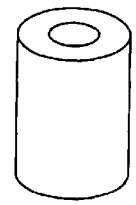
FIG. 10        FIG. 11        FIG. 12
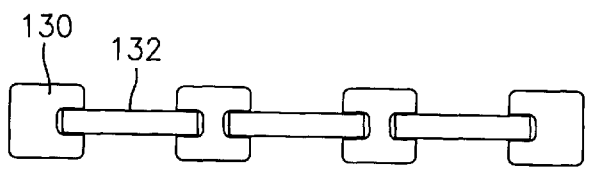
FIG. 13
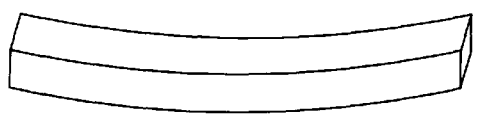
FIG. 14
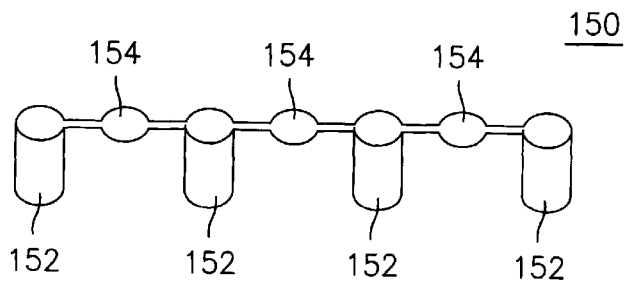
FIG. 15

PREFABRICATED COMPONENTS FOR DENTAL APPLIANCES

CROSS-REFERENCE TO RELATED APPLICATIONS

This is a continuation-in-part application of application Ser. No. 09/059,492 filed Apr. 13, 1998 entitled PREFABRICATED COMPONENTS FOR DENTAL APPLIANCES, now abandoned.

TECHNICAL FIELD

The present invention relates generally to dental appliances and restorations and more particularly to prefabricated components for use in dental appliances and restorations and methods of manufacture thereof.

BACKGROUND OF THE INVENTION

Dental appliances and restorations such as bridges, crowns, dentures and the like may be used to restore a missing tooth and retain natural teeth in position and prevent migration subsequent to orthodontic treatment. Structural components used in these appliances often include wires, bars, posts, shells, beams, clasps and other shapes. The shape of the structural components may vary depending upon the requirements of the appliance.

The manufacture of frameworks for bridges using current techniques can be time consuming and labor intensive. Some techniques may involve taking uncured fiber-reinforced composite material and forming uncured strips of the fiber-reinforced composite material into a bridge framework upon a dental cast. The procedure can be an involved and complex process depending upon the final shape desired. Moreover, dental technicians and practitioners may use less than the optimum amount of fiber for reinforcement when preparing the dental framework in order to reduce the cost which may lead to low strength and therefore potential fracture of the final product. Furthermore, the complexity of the dental appliance may require a certain dexterity to achieve optimal properties that may not be achievable by some technicians and practitioners. The use of metals, alloys and ceramics which exhibit high flexural strengths such as 300 MPa and higher reduces light transmission and thus affects the aesthetic appearance.

There remains a need to simplify the process of fabricating dental appliances to reduce time and labor involved in the preparation process and to provide appliances having optimum properties. It is desirable to reduce the risk of contamination during the fabrication of dental appliances. It is desirable to maintain strength of dental appliances without sacrificing aesthetic and light transmitting properties.

SUMMARY OF THE INVENTION

These and other objects and advantages are accomplished by the present invention wherein preshaped, prefabricated cured components are prepared in a variety of shapes and sizes to be used in the fabrication of dental appliances. Preferably the components are fabricated of a fiber-reinforced composite material comprising fibers impregnated with a polymeric matrix. After impregnation of a fibrous material with a polymeric matrix, the resultant fiber-reinforced composite material is shaped and is partially or fully cured to the point of sufficient hardness to provide a component for use in the fabrication of dental appliances including but not limited to orthodontic retainers, bridges, space maintainers, tooth replacement appliances, dentures, crowns, posts, jackets, inlays, onlays, facings, veneers, facets, implants, abutments and splints.

In one embodiment of the present invention, the components are in the shape of a structure for immediate use in the fabrication of a dental appliance. The structural components are formed into any known shapes useful in the fabrication of a dental appliance or restoration. Preferably, the structural components are in the shape of bars or pontics. The pontics have interproximal extensions and may be single unit or multiple unit useful in the fabrication of frameworks for bridges. The structural components may be "ready-to-use" for immediate use in the fabrication of a dental appliance or restoration or may be further modified, for example by cutting, carving or grinding prior to using in the fabrication of a dental appliance or restoration.

In another embodiment of the present invention, the components are formed into pieces or blocks of fiber-reinforced composite material. The blocks of material are useful in making a variety of shapes and sizes and may be modified by a variety of methods including but not limited to machining, carving, cutting, grinding, etching and abrading.

The bars, pontics and blocks may be of any cross-sectional configuration effective to provide strength and stiffness to the finished dental appliance.

In the method of the present invention, the components are made after the impregnation of the fibers with a polymeric matrix. After impregnation of the fibers, the resultant composite material is formed into, for example, a long bar and cured or polymerized to a hardness whereby the bar may be cut and/or machined without deforming the structural integrity of the bar. The bar is preferably cut into short segments and is ready for use in the fabrication of dental appliances. The bars may be used as is or may be further modified by cutting, grinding, machining, and the like to provide a specifically shaped or customized component. The component may further be veneered with particulate-filled composite to develop clinically acceptable anatomy.

BRIEF DESCRIPTION OF THE DRAWINGS

Features of the present invention are disclosed in the accompanying drawings, wherein similar reference characters denote similar elements throughout the several views, and wherein:

FIG. 7 is a perspective view of a cylindrical block formed in accordance with the present invention;

FIG. 8 is a perspective view of a tooth machined out of the block shown in FIG. 7;

FIG. 9 is a perspective view of a rectangular block formed in accordance with the present invention;

FIG. 10 is a perspective view of a bridge machined out of the block shown in FIG. 9;

FIG. 11 is a perspective view of a square block formed in accordance with the present invention;

FIG. 12 is a perspective view of a cylinder machined out of the block shown in FIG. 11;

FIG. 13 is a perspective view of a partial implant system formed from structural components of the present invention;

FIG. 14 is a perspective view of a curved rectangular block formed in accordance with the present invention; and FIG. 15 is a perspective view of an implant superstructure machined out of the block shown in FIG. 14.

DETAILED DESCRIPTION

Figure 1A:
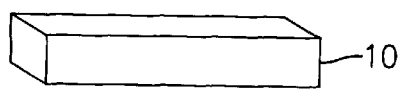
FIG. 1 is a perspective view of bars of different shapes that may be formed in accordance with the present invention.
Figure 1B:
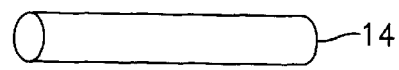
Figure 1C:
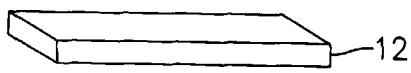
Figure 1D:
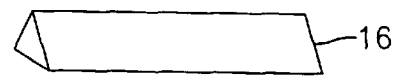

The prefabricated components in accordance with the present invention are preferably formed from a fiber-reinforced composite material comprising a polymeric matrix and reinforcing fibers within the matrix. The fibers are embedded in the matrix manually or mechanically by a variety of techniques including, but not limited to matched die processes, autoclave molding, resin injection molding (RIM), sheet, dough and bulk molding, press molding, injection molding, reaction injection molding, resin transfer molding (RTM), compression molding, open molding, extrusion, pultrusion and filament winding. U.S. Pat. Nos. 4,717,341 and 4,894,012 to Goldberg et al. show methods of impregnation and are hereby incorporated by reference. Due to the impregnation method used, the fiber distribution is approximately uniform, but most importantly all fibers are thoroughly wetted by the resin which forms the polymeric matrix and there are no apparent voids at the fiber-resin interface. Preferably the fiber-reinforced polymeric matrix is formed using the pultrusion or filament winding technique. The polymeric matrix element of the composite is selected from those known in the art of dental materials, including but not being limited to polyamides, polyesters, polyolefins, polyimides, polyarylates, polyurethanes, vinyl esters or epoxy-based materials. Other polymeric matrices include styrenes, stryrene acrylonitriles, ABS polymers, polysulfones, polyacetals, polycarbonates, polyphenylene sulfides, and the like.

Preferred polymeric materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; commonly assigned U.S. Pat. Nos. 5,276,068 and 5,444,104 to Waknine; and commonly assigned U.S. Pat. No. 5,684,103 to Jia et al., the pertinent portions of all which are herein incorporated by reference. An especially preferred methacrylate monomer is the condensation product of bisphenol A and glycidyl methacrylate, 2,2'-bis[4-(3-methacryloxy-2-hydroxypropoxy)-phenyl]-propane (hereinafter abbreviated "BIS-GMA"). Polyurethane dimethacrylates (hereinafter abbreviated "PUDMA"), triethylene glycol dimethacrylate (hereinafter abbreviated "TEGDMA"), polyethylene glycol dimethacrylate (hereinafter abbreviated "PEGDMA"), polycarbonate dimethacrylate (hereinafter abbreviated "PCDMA") and ethoxylated bisphenol A dimethacrylate (hereinafter abbreviated "EBPADMA") are also commonly-used principal polymers suitable for use in the present invention.

The polymer matrix typically includes polymerization initiators, polymerization accelerators, ultraviolet light absorbers, anti-oxidants, and other additives well known in the art. The polymer matrices may be visible light curable, self-curing, dual curing, and vacuum, heat, and pressure curable compositions as well as any combination thereof. The visible light curable compositions include the usual polymerization initiators, polymerization accelerators, ultraviolet absorbers, fluorescent whitening agents, and the like. Preferred light curing initiators include camphorquinone (CQ) and trimethyl benzoyl phosphine oxide (TPO). The heat curable compositions, which are generally filled compositions, include, in addition to the monomeric components, a heat cure initiator such as benzoyl peroxide, 1,1'-azobis(cyclohexanecarbo-nitrile), or other free radical initiators. The preferred polymeric matrix is a curable matrix, wherein light cure effects partial cure of the matrix, and final curing is by heat under controlled atmosphere.

The polymeric matrix may further comprise at least one filler known in the art and used in dental restorative materials, the amount of such filler being determined by the specific use of the fiber-reinforced composite. Generally, no or relatively little additional filler is present in the polymeric matrix, i.e., up to thirty percent by weight of the composite. Suitable fillers are those capable of being covalently bonded to the polymeric matrix itself or to a coupling agent that is covalently bonded to both. Examples of suitable filling materials include but are not limited to those known in the art such as silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania. Particularly suitable fillers for dental filling-type materials prepared in accordance with this invention are those having a particle size ranging from about 0.1–5.0 microns with a silicate colloid of 0.001 to about 0.07 microns and may be prepared by a series of milling steps comprising wet milling in an aqueous medium, surface etch milling and dry or wet silanation. Some of the aforementioned inorganic filling materials are disclosed in commonly-assigned U.S. Pat. Nos. 4,544,359 and 4,547,531 to Waknine, the pertinent portions of which are incorporated herein by reference.

The reinforcing fiber element of the composite preferably comprises glass, carbon, graphite, polyaramid, or other fibers known in the art, such as polyesters, polyamides, and other natural and synthetic materials compatible with the polymeric matrix. Some of the aforementioned fibrous materials are disclosed in commonly assigned copending U.S. patent application Ser. Nos. 08/907,177, 09/059,492, 60/055,590, 08/951,414 and U.S. Pat. Nos. 4,717,341 and 4,894,012 all which are incorporated herein by reference. The fibers may further be treated, for example, chemically or mechanically etched and/or silanized, to enhance the bond between the fibers and the polymeric matrix. The fibers preferably take the form of long, continuous filaments, although the filaments may be as short as 0.1 to 4 millimeters. Shorter fibers of uniform or random length might also be employed. Preferably, the fibers are at least partially aligned and oriented along the longitudinal dimensions of the wire. However, depending on the end use of the composite material, the fibers may also be otherwise oriented, including being normal or perpendicular to that dimension. The fibrous element may optionally take the form of a fabric. Fabric may be of the woven or non-woven type and is preferably preimpregnated with a polymeric material as set forth above. Examples of suitable woven fabric materials include but are not limited to those known in the art such as E glass and S glass fabrics and reinforcement fabrics sold by NFGS Inc. of New Hampshire under the style numbers 6522 and 7581. One preferred non-woven fabric material is available under the name Glass Tissue (20103A) from Technical Fibre Products Ltd. of Slate Hill, N.Y. The fibrous component may be present in the fiber reinforced composite material in the range from about 20% to about 85%, and more preferably between about 30% to about 65% by weight.

Fabric may also be combined with the fiber-reinforced composite material to produce a high strength appliance. Fabric may be of the woven or non-woven type as discussed above and is preferably preimpregnated with a polymeric material. Suitable polymeric materials are those listed above as polymeric matrix materials.

In accordance with one embodiment of the present invention, the fiber-reinforced polymeric composite material is preformed into structural components to provide ready-to-use units for use in the fabrication of dental appliances. The structural components are formed into any known shape(s) useful in the fabrication of a dental appliance or restoration. Preferably, the structural components are in the shape of bars or pontics. The pontics have interproximal extensions and may be single unit or multiple unit useful in the fabrication of frameworks for bridges. The bars and pontics may be straight or curved depending on the end use. The structural components may be "ready-to-use" for immediate use in the fabrication of a dental appliance or restoration or may be further modified, for example by cutting, carving or grinding prior to using in the fabrication of a dental appliance or restoration.

FIG. 1 shows various shapes of bars formed in accordance with the present invention. FIGS. 1A through 1D depict bars of square 10, circular 12, rectangular 14 and triangular 16 cross-section, respectively. Structural components in the form of bars are typically used in the manufacture of dental bridges or posts. If posts are desired, the cross-sectional dimension of the post must be narrow enough to fit within the root canal.

Figure 5:
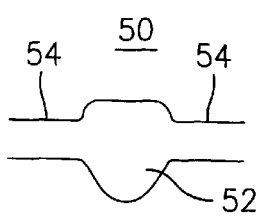
FIG. 5 is a front elevational view of a single unit pontic formed using a mold in FIG. 4.

More complicated shapes of preformed structural components may be formed from the structural bars either manually or mechanically by carving, cutting, grinding, machining or using other similar means. The complicated shapes may include pontics of varying lengths and shapes as noted above and as shown in FIGS. 2, 3 and 5, but are not limited to the specific shapes shown. Alternatively, the complicated shapes may be formed by pressing composite material into molds and fully or partially curing into a hardness sufficient to withstand cutting, carving or machining. In a preferred embodiment, preformed structural bars are placed within a series of molds and composite material is filled into the cavities surrounding the bars to form a single unit pontic 50 as shown in FIG. 5.

Figure 2:
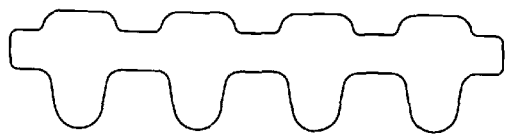
FIG. 2 is a front elevational view of a multi-unit pontic formed in accordance with the present invention.
Figure 3:
FIG. 3 is a top plan view of a multi-unit pontic formed in accordance with the present invention.

FIG. 2 shows a multiple unit pontic 20 that may be used in the preparation of an anterior bridge. FIG. 3 displays a multiple unit pontic 30 that could be used in the preparation of a bridge.

Figure 4:
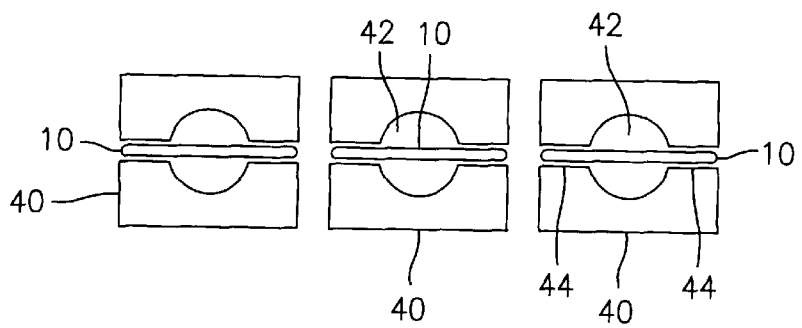
FIG. 4 is a top plan view of a series of molds used to fabricate single unit pontics in accordance with the present invention.
Figure 6:
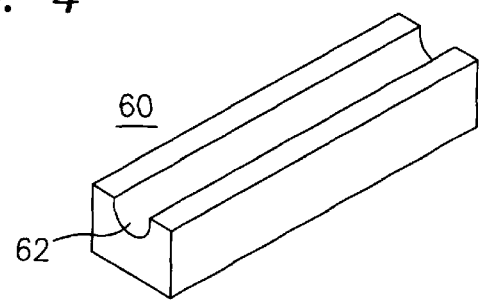
FIG. 6 is a side elevational view of a mold used to fabricate long bars in accordance with the present invention.

FIG. 4 depicts a series of molds 40 having cavities 42 therein connected to laterally extending thin sections 44. FIG. 6 shows a single mold 60 have a longitudinally extending cavity 62 used to fabricate a long bar that may be cut into smaller sections after it has cured. In accordance with one process of the present invention, one or more layers of filled composite material may be poured into cavities 42. Preferred composite materials are available from JENERIC/PENTRON Inc., Wallingford, Conn., under the trademarks FLOW-IT and LUTE-IT. One or more layers of pre-impregnated woven or nonwoven fabric may be placed on the composite layer(s). Alternately, the fabric may be first placed in the cavities 42 and composite material may be deposited thereover. After the composite and/or fabric is provided in cavities 42, preformed structural bars 10 may be placed within mold 40 as shown. More composite material may be used to fill any voids in cavities 42. The material is cured to form a structural component in the shape of a single unit pontic 50 having a central pontic section 52 and laterally extending arms 54. Preferably, the molded component is cured to a sufficient hardness whereby it may be machined or carved to a desired final shape by the technician or dentist during fabrication of the dental appliance. The molded component may be partially cured at the time of fabrication and the curing can be completed at the time of fabrication of the dental appliance or the molded component may be fully cured at the time of manufacture thereof. Mold 60 may be used in a similar fashion to molds 40 to prepare a long bar that may cut into smaller sections after it has cured.

In another embodiment of the present invention, the components are formed into pieces or blocks of fiber-reinforced composite material. The blocks of material may be of a variety of shapes and sizes and may be modified by a variety of methods including but not limited to machining, carving, cutting, grinding, abrading or etching.

FIGS. 7, 9 and 11 depict blocks formed in accordance with the present invention. FIG. 7 shows a cylindrical block, FIG. 9 shows a rectangular block and FIG. 11 shows a square block. FIG. 8 depicts a tooth which has been machined from the block shown in FIG. 7. FIG. 10 shows a bridge machined from the block in FIG. 9. FIG. 12 shows a cylinder for use is an implant machined from the block in FIG. 11.

The cylinder shown in FIG. 12 can be used in combination with prefabricated bars of the present invention or may be used with uncured fiber-reinforced composite material such as Fiberkor® available from Jeneric/Pentron Inc., Wallingford, Conn. An implant may be manufactured with one or all of its components fabricated from the structural components of the present invention including but not limited to the abutments, cylinders and framework. The resulting implant components provide good shock absorbancy. Preferably the implant components are machined out of blocks fabricated in accordance with the present invention. The machined blocks may include retentive designs on the eternal service for proper linkage to create multi-unit bridges or to reinforce bonding to the overlay composite materials. The implant superstructure may additionally include pontic components for proper support of the overlay material. FIG. 13 shows a partial implant system wherein cylinders 130 and bars 132 are disposed therebetween to form the superstructure. Cylinders 130 are preferably machined from blocks made in accordance with the present invention. Bars 132 are likewise manufactured in accordance with the present invention.

FIG. 14 shows a curved rectangular block formed in accordance with the present invention. FIG. 15 shows an implant superstructure 150 which has been machined from the block shown in FIG. 14. Superstructure 150 comprises cylinders 152 interconnected with pontic sections 154.

In accordance with the method of the present invention, the components may be manufactured on line as part of the fiber impregnation process or may be molded into shapes after the impregnation process. In a preferred embodiment of the invention, components in the form of, for example, bars or blocks may be manufactured following the process of fiber impregnation with a matrix material. The bars or blocks are preferably formed under pressure and undergo either full or partial polymerization to impart specific properties for specific applications. Long, continuous bars or blocks may be molded and cured to a hardness sufficient to withstand cutting, carving or machining and subsequently cut into the desired lengths at the time of manufacture or at some point thereafter. The cross-section of the structural components may be square, rectangular, triangular, rhomboidal, ovoidal, tapered, cylindrical, or of any other cross-sectional configuration effective to provide strength and stiffness to the finished dental appliance. The dimensions may be of varying lengths, widths and heights and the shades thereof may be of any shade suitable for dental materials. Coloring agents known in the art may be added to the polymeric matrix material prior to curing.

The components may be used as frameworks or understructures for crowns, bridges, implant abutment cylinders, implant superstructures and the like. The framework/understructure can be made from the structural components in a variety of ways. The method of fabrication may be manual or automated. In the manual method, a technician can select a component of, for example, rectangular shape. The technician cuts the block to proper dimension and size and carves out the desired anatomical features using standard laboratory tools.

To perform the procedure by automated or mechanical means, an apparatus such as a CAD/CAMming machine is used to automatically shape the structural component into the form or contour desired. The component is preferably in the form of a block (also known as a blank) for CAD/CAMming purposes. The technicians and/or practitioners collect three dimensional data regarding the final desired shape of the dental appliance or restoration and machine or mill the block or blank to achieve the final desired shape. The data may be collected from actual teeth, implants, etc. or from models or prefabricated frameworks (of wax, duralay, etc.) prepared on teeth or stone models or from an impression taken of the tooth or teeth to be corrected by using a scanning device such as the Pro-Scan™ device available from IntraTech in Irving, Tex. The data may be used as is or may be modified using computer software. Based on the data, the blank is machined via CAM to a three-dimensional dental appliance or material. The CAD/CAM process may be performed at one location or the CAD data may be transferred via modem or electronic transmission to another location where computer assisted machining or milling is performed. The machined part may be further modified or treated with for example, a surface treatment such as abrasion, etching, or silanation, or with a special bonding agent. Additionally, the machined part can be joined with other preimpregnated fiber-reinforced materials prior to being overlaid with a coating or veneer. The veneer may be a particulate-filled composite material such as commerically available Sculpture® material available from Jeneric/Pentron Inc., Wallingford, Conn. and is preferably applied to the machined or manually carved part to provide the final anatomy. The finished appliance or restoration can either be bonded or mechanically anchored. Bonding is the preferred fastening means.

The prefabricated, preshaped cured components of the present invention can substantially eliminate operator induced errors, greatly save time and enhance overall properties and longevity of final restorations. For implant restorations, replacement of the rigid (high modulus) metal components with a lower modulus material of the fiber-reinforced composite structural components, improves shock absorption.

As will be appreciated, the present invention provides preshaped, prefabricated cured components having optimum strength. The components may be ready-to-use structural components, structural components which may or may not be further modified prior to use, or components which must be further modified prior to use. The components are provided of varying shapes and sizes offering many options to the technician or practitioner in the fabrication of dental appliances. Due to the many different shapes, sizes and contours of teeth, a kit may be provided including ready-to-use structural components in the shape of pontics and bars of varying configurations and sizes to offer the technician and practitioner options with which to construct dental appliances. Accordingly, custom made dental appliances can be easily fabricated using the ready-to-use structural components. The ready-to-use components may be further modified prior to fabrication of a dental appliance or restoration. Kits may also be provided with component blocks of varying shapes, sizes and colors offering many options to the technician and practitioner.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A ready-to-use pontic for use in the fabrication of a dental appliance system wherein the pontic comprises one or more pontic sections and one or more sets of interpoximal extensions extending through and out of the pontic sections and comprising:

a prefabricated preshaped cured fiber-reinforced composite material comprising a polymeric matrix which is formed from a resin, a filler component, and a reinforcing fiber component;

wherein the fiber-reinforced composite material comprises fibers distributed uniformly in the resin and wherein all the fibers are thoroughly wetted by the resin; and wherein the fiber reinforced composite material is shaped and cured to a hardness for use in the dental appliance system.

2. The pontic of claim 1 wherein the fiber-reinforced composite is structurally shaped for immediate use in dental appliance systems.

3. The pontic of claim 1 wherein the component is modified by machining, cutting or carving.

4. The pontic of claim 1 wherein the shape of the cross-section of the interproximal extensions is selected from the group consisting of a square, rectangle, triangle, rhomboid, ovoid, and cylinder.

5. The component of claim 1 wherein the pontic is either curved or straight.

6. The pontic of claim 1 wherein the fiber-reinforced composite material has undergone full polymerization.

7. The pontic of claim 1 wherein the dental appliance system is selected from the group consisting of orthodontic retainers, bridges, space maintainers, tooth replacement appliances, splints, crowns, partial crowns, dentures, posts, teeth, jackets, inlays, onlays, facings, veneers, facets, implants, cylinders, abutments and connectors.

8. The pontic of claim 1 further including a coating thereon.

9. The pontic of claim 1 wherein the fiber-reinforced composite material further includes one or more layers of composite material.

10. The pontic of claim 1 further including a constituent selected from the group of woven fabric, nonwoven fabric and mixtures thereof.

11. The pontic of claim 10 wherein the fabric is preimpregnated with a polymeric material.

12. A dental restoration which comprises the component of claim 1.

13. The dental restoration of claim 12 selected from the group consisting of orthodontic retainers, bridges, space maintainers, tooth replacement appliances, splints, crowns, partial crowns, dentures, posts, teeth, jackets, inlays, onlays, facings, veneers, facets, implants, abutments, cylinders, and connectors.

14. An implant system comprising one or more sections manufactured from the components of claim 1.

15. A kit for the fabrication of a dental appliance comprising:
   one or more ready-to-use components wherein the one or more ready-to-use components comprises a prefabricated preshaped cured fiber-reinforced composite material comprising a polymeric matrix, a filler component, and a reinforcing fiber component;
   wherein the one or more ready-to-use components comprise pontics;
   wherein the pontics comprise one or more pontic sections and one or more sets of interpoximal extensions extending through and out of the pontic sections and comprising a prefabricated preshaped cured fiber-reinforced composite material comprising a polymeric matrix which is formed by a resin, a filler component, and a reinforcing fiber component;
   wherein the fiber-reinforced composite material comprises fibers distributed uniformly in the resin and wherein all the fibers are thoroughly wetted by the resin; and
   wherein the fiber reinforced composite material is shaped and cured to a hardness for use in the dental appliance system.

16. The kit of claim 15 wherein the components further comprise bars.

17. The kit of claim 16 wherein the bars and pontics are of a variety of different shades.

18. The kit of claim 15 wherein the components further comprise blocks.

19. The kit of claim 18 wherein the blocks are of a variety of different dimensions and different cross-sectional configurations.

20. The kit of claim 18 wherein the blocks are of a variety of different shades.

21. The kit of claim 15 wherein the pontics are single unit and multiple unit pontics.

22. The kit of claim 15 wherein the bars and pontics are of a variety of different dimensions and different cross-sectional configurations.

23. The kit of claim 15 further comprising composite material, fiber-reinforced composite material and filler material.

24. A dental restoration comprising:
   a pontic for use in the fabrication of a dental appliance system wherein the pontic comprises one or more pontic sections and one or more sets of interpoximal extensions extending through and out of the pontic sections and comprising a prefabricated preshaped cured fiber-reinforced composite material comprising a polymeric matrix which is formed by a resin, a filler component, and a reinforcing fiber component;
   wherein the fiber-reinforced composite material comprises fibers distributed uniformly in the resin and wherein all the fibers are thoroughly wetted by the resin.

25. The dental restoration of claim 24 wherein the pontic is modified prior to the incorporation into the dental restoration.

26. A blank for the manufacture of a dental restoration comprising:
   a prefabricated preshaped cured fiber-reinforced composite material comprising a polymeric matrix which is formed by a resin, a filler component, and a reinforcing fiber component, wherein the fiber-reinforced composite material comprises fibers distributed uniformly in the resin and wherein all the fibers are thoroughly wetted by the resin; and wherein the fiber-reinforced composite material is shaped and cured for use in a CAD/CAM system.

27. An implant system comprising one or more sections manufactured from the blanks of claim 26.

28. The implant system of claim 27 wherein sections comprise abutments, cylinders, and frameworks.

29. A dental restoration manufactured from the blank of claim 26.

30. A ready-to-use component for use in a CAD/CAM system comprising:
   a prefabricated preshaped cured fiber-reinforced composite material comprising a polymeric matrix which is formed by a resin, a filler component, and a reinforcing fiber component whereby the fibers are impregnated with the polymeric matrix and filler component, and wherein the fiber-reinforced composite material comprises fibers distributed uniformly in the resin and wherein all the fibers are thoroughly wetted by the resin, and thereafter formed into shapes under pressure; and
   wherein the fiber-reinforced composite material is shaped and cured for use in the CAD/CAM system.

31. A method of making a dental restoration comprising:
   putting a ready-to-use structural component onto a dental cast, the structural component comprising a prefabricated preshaped cured fiber-reinforced composite material comprising a polymeric matrix which is formed by a resin, a filler component, and a reinforcing fiber component, wherein the fiber-reinforced composite material comprises fibers distributed uniformly in the resin, wherein all the fibers are thoroughly wetted by the resin, and wherein the fiber-reinforced composite material is shaped and cured to a hardness for use in the dental restoration;
   adding one or more layers of composite material thereon; and
   curing the one or more layers of composite material.

32. The method of claim 31 wherein the structural component is modified by machining, cutting or carving prior to the step of adding one or more layers of material thereon.

33. A method of making a dental restoration comprising:

fabricating a fiber-reinforced composite material into a shaped component wherein the fiber-reinforced composite material comprises a polymeric matrix which is formed by a resin, a filler component, and a reinforcing fiber component, wherein the fiber-reinforced composite material comprises fibers distributed uniformly in the resin, wherein all the fibers are thoroughly wetted by the resin, and whereby the fibers are impregnated with the polymeric matrix and filler component and formed into shapes under pressure;

curing the shaped component to provide a prefabricated, shaped, cured component; and milling the component under the control of a CAD/CAM system to provide a dental appliance.

\* \* \* \* \*